US011259911B2

(12) United States Patent
Shahriari

(10) Patent No.: US 11,259,911 B2
(45) Date of Patent: Mar. 1, 2022

(54) BRANCHED AORTIC GRAFT AND METHOD OF USING THE SAME

(71) Applicant: Ascyrus Medical, LLC, Boca Raton, FL (US)

(72) Inventor: Ali Shahriari, Boca Raton, FL (US)

(73) Assignee: ASCYRUS MEDICAL, LLC, Boca Raton, FL (US)

( * ) Notice: Subject to any disclaimer, the term of this patent is extended or adjusted under 35 U.S.C. 154(b) by 382 days.

(21) Appl. No.: 15/836,359

(22) Filed: Dec. 8, 2017

(65) Prior Publication Data

US 2018/0098837 A1     Apr. 12, 2018

Related U.S. Application Data

(63) Continuation of application No. PCT/US2016/038437, filed on Jun. 20, 2016.
(Continued)

(51) Int. Cl.
*A61F 2/07* (2013.01)
*A61F 2/95* (2013.01)
(Continued)

(52) U.S. Cl.
CPC .................. *A61F 2/07* (2013.01); *A61F 2/95* (2013.01); *A61F 2/2433* (2013.01); *A61F 2/86* (2013.01);
(Continued)

(58) Field of Classification Search
CPC ...... A61F 2/07; A61F 2/954; A61F 2002/061; A61F 2002/067; A61F 2002/068;
(Continued)

(56) References Cited

U.S. PATENT DOCUMENTS 5,976,179 A    11/1999 Inoue
6,331,188 B1   12/2001 Lau et al.
(Continued)

FOREIGN PATENT DOCUMENTS

EP     2740441 A1    6/2014
JP     2011502628 A   1/2011
(Continued)

OTHER PUBLICATIONS

JPO, Office Action for Japanese Patent Application No. 2018-206631, dated Oct. 23, 2019, 9 pages.
(Continued)

*Primary Examiner* — Kathleen S Holwerda
(74) *Attorney, Agent, or Firm* — Meunier Carlin & Curfman LLC

(57) ABSTRACT

A device and method for repair of a patient's aorta is disclosed. The device includes a first component including an outer diameter equal to a first diameter, a second component attached to a distal end of the first component, and a plurality of third components positioned in a chamber defined in the second component. The second component includes a proximal surface extending outwardly from the distal end of the first component, and a plurality of openings defined in the proximal surface. Each third component includes a passageway extending inwardly from an opening of the plurality of openings defined in the proximal surface. Each passageway is sized to receive a tubular conduit, and the proximal surface has an outer edge that defines a second diameter greater than the first diameter.

16 Claims, 10 Drawing Sheets

Related U.S. Application Data

(60) Provisional application No. 62/181,242, filed on Jun. 18, 2015.

(51) Int. Cl.
| | | |
|---|---|---|
| *A61F 2/89* | (2013.01) | |
| *A61F 2/24* | (2006.01) | |
| *A61F 2/86* | (2013.01) | |
| *A61F 2/954* | (2013.01) | |
| *A61F 2/06* | (2013.01) | |

(52) U.S. Cl.
CPC ............. *A61F 2/89* (2013.01); *A61F 2/954* (2013.01); *A61F 2002/061* (2013.01); *A61F 2002/067* (2013.01); *A61F 2002/068* (2013.01); *A61F 2002/075* (2013.01); *A61F 2230/0067* (2013.01); *A61F 2230/0078* (2013.01); *A61F 2250/0037* (2013.01); *A61F 2250/0039* (2013.01); *A61F 2250/0098* (2013.01)

(58) Field of Classification Search
CPC ........ A61F 2002/075; A61F 2/89; A61F 2/95; A61F 2/86–97; A61F 2/2433; A61F 2250/0098
See application file for complete search history.

(56) References Cited

U.S. PATENT DOCUMENTS

| | | | |
|---|---|---|---|
| 6,409,750 B1 | 6/2002 | Hyodoh et al. | |
| 6,656,219 B1 | 12/2003 | Wiktor | |
| 6,723,116 B2 | 4/2004 | Taheri | |
| 6,814,752 B1* | 11/2004 | Chuter | A61F 2/07 623/1.27 |
| 6,918,925 B2 | 7/2005 | Tehrani | |
| 7,488,344 B2 | 2/2009 | Hartley et al. | |
| 8,603,156 B2 | 12/2013 | Hartley et al. | |
| 8,747,455 B2 | 6/2014 | Greenberg | |
| 8,945,203 B2 | 2/2015 | Shalev et al. | |
| 2002/0177890 A1 | 11/2002 | Lenker | |
| 2003/0199967 A1* | 10/2003 | Hartley | A61F 2/07 623/1.13 |
| 2005/0090834 A1 | 4/2005 | Chiang et al. | |
| 2005/0102018 A1* | 5/2005 | Carpenter | A61F 2/07 623/1.11 |
| 2006/0089704 A1 | 4/2006 | Douglas | |
| 2006/0247760 A1 | 11/2006 | Ganesan et al. | |
| 2007/0168013 A1 | 7/2007 | Douglas | |
| 2008/0140110 A1 | 6/2008 | Spence | |
| 2009/0099650 A1 | 4/2009 | Bolduc et al. | |
| 2009/0319017 A1 | 12/2009 | Berez et al. | |
| 2009/0319022 A1* | 12/2009 | Hartley | A61F 2/07 623/1.13 |
| 2010/0114291 A1 | 5/2010 | Kolbel et al. | |
| 2011/0257731 A1* | 10/2011 | Hartley | A61F 2/07 623/1.35 |
| 2012/0179236 A1 | 7/2012 | Benary et al. | |
| 2012/0296414 A1* | 11/2012 | Hartley | A61F 2/07 623/1.13 |
| 2012/0323300 A1 | 12/2012 | Greenberg et al. | |
| 2013/0013053 A1* | 1/2013 | Hartley | A61F 2/06 623/1.13 |
| 2013/0144373 A1 | 6/2013 | Shahriari | |
| 2013/0166015 A1 | 6/2013 | Roeder | |
| 2013/0211506 A1 | 8/2013 | Dake et al. | |
| 2013/0289713 A1 | 10/2013 | Pearson et al. | |
| 2014/0046428 A1 | 2/2014 | Cragg et al. | |
| 2014/0172064 A1 | 6/2014 | Kelly | |
| 2014/0257464 A1 | 9/2014 | Roeder | |
| 2014/0277348 A1 | 9/2014 | Roeder | |
| 2014/0316513 A1 | 10/2014 | Tang | |
| 2015/0148890 A1 | 5/2015 | Hartley et al. | |

FOREIGN PATENT DOCUMENTS

| | | |
|---|---|---|
| WO | 0187180 A2 | 11/2001 |
| WO | 2005087117 A1 | 9/2005 |
| WO | 2010105195 A2 | 9/2010 |
| WO | 2014141232 A1 | 9/2014 |

OTHER PUBLICATIONS

EPO, Supplementary European Search Report for European Patent No. EP16735541, dated Jul. 11, 2018.
ISA/KR, International Search Report and Written Opinion of PCT Patent Application No. PCT/US2016/038437, dated Sep. 12, 2016.
WIPO, International Preliminary Report on Patentability of PCT Patent Application No. PCT/US2016/038437, dated Dec. 19, 2017.
EPO, Extended European Search Report for European Patent Application No. 16812646.4, dated Jan. 17, 2019.
EPO, Extended European Search Report in European Patent Application No. 16743828.2 dated Sep. 25, 2018.

\* cited by examiner

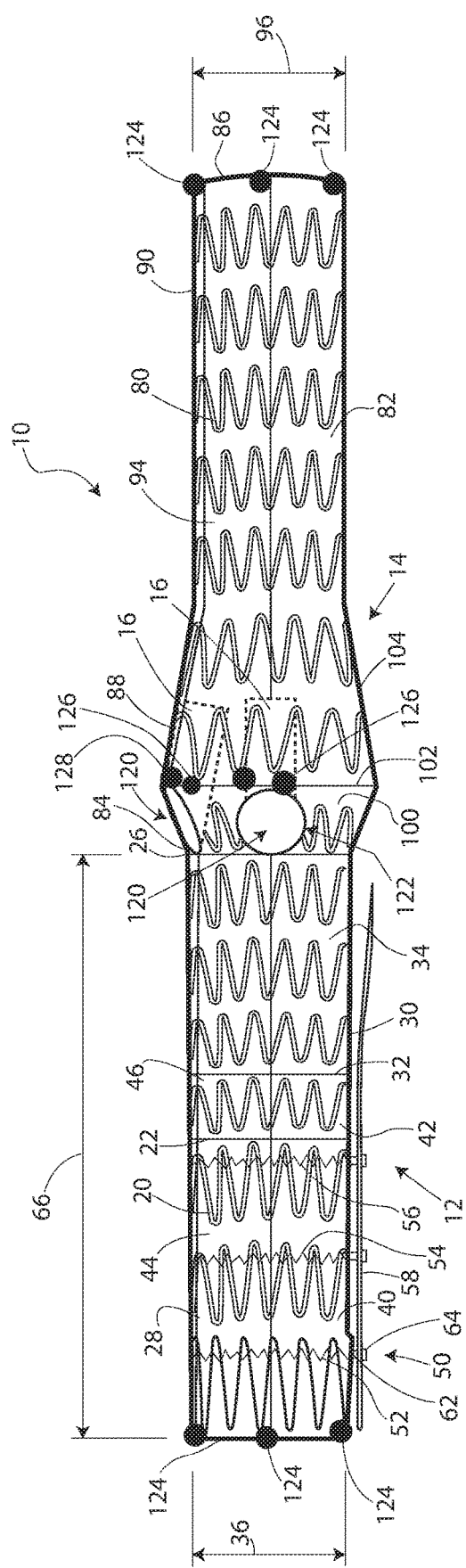

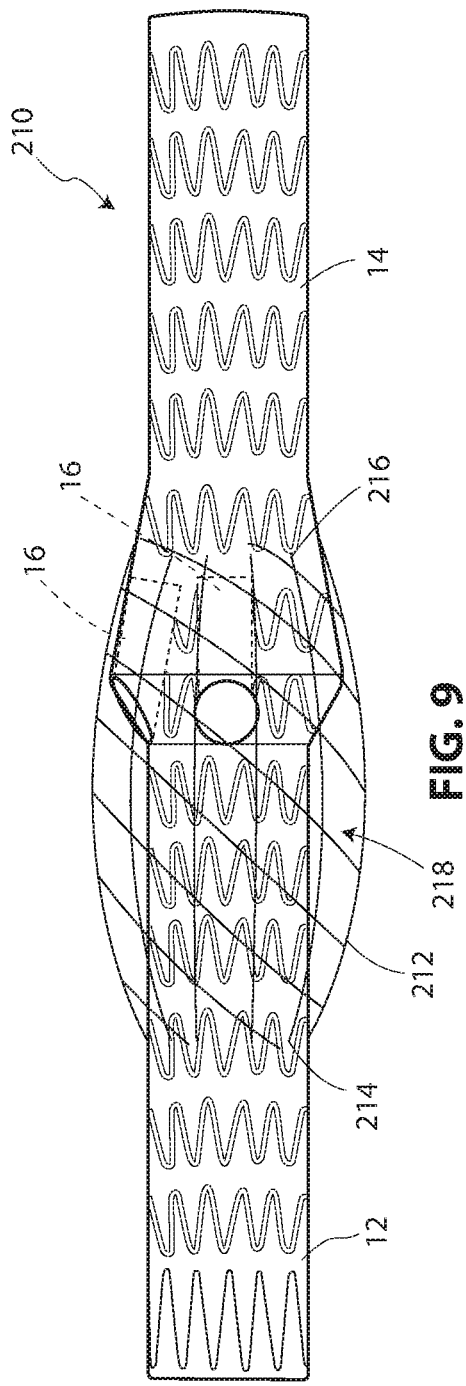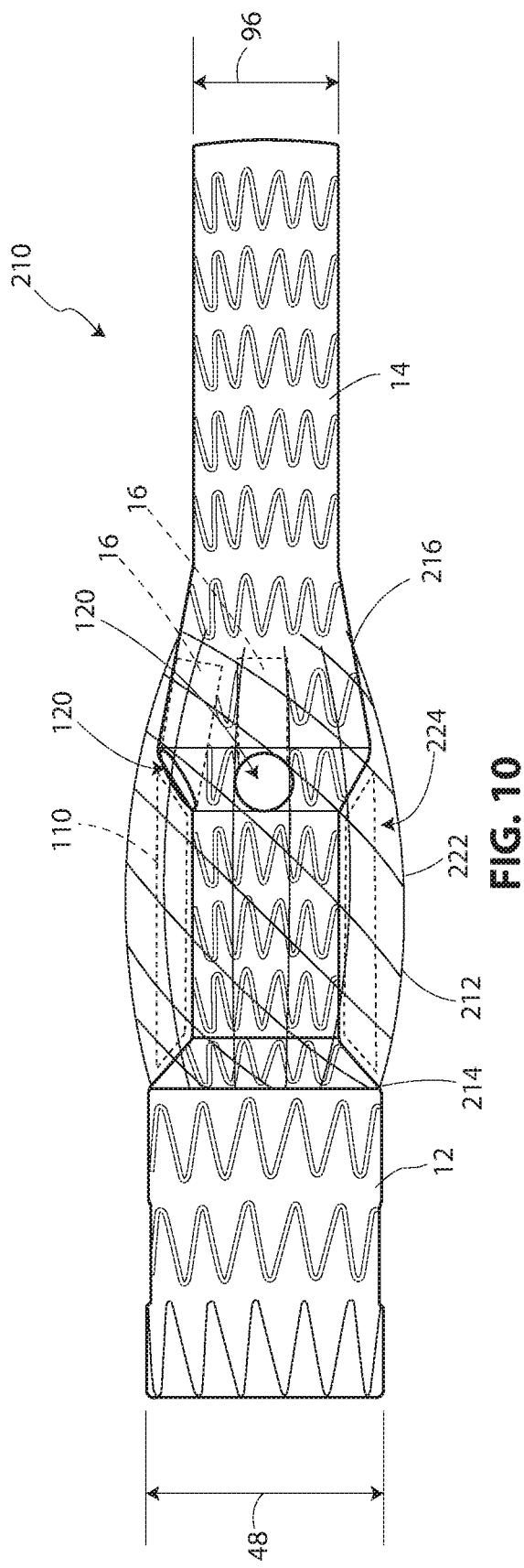

BRANCHED AORTIC GRAFT AND METHOD OF USING THE SAME

CROSS-REFERENCE TO RELATED APPLICATIONS

This application is a continuation of PCT Patent Application No. PCT/US2016/038437 filed on Jun. 20, 2016 and entitled "BRANCHED AORTIC GRAFT AND METHOD OF USING THE SAME", which claims priority to U.S. Provisional Patent Application No. 62/181,242 filed on Jun. 18, 2015 and entitled "BRANCHED AORTIC GRAFT AND METHOD OF USING THE SAME", the entire contents of which are all incorporated herein by reference.

TECHNICAL FIELD

The present disclosure relates to designs for aortic grafts and, more specifically, to an aortic graft design for endovascular repair of aneurysms in the aortic arch and the paravisceral aorta.

BACKGROUND

The aortic arch is the anatomical region of the aorta located between the ascending aorta and the descending aorta. The aortic arch gives rise to the supra-aortic branches supplying blood flow to the upper extremities and the two hemispheres of the brain. The arch may be involved with different disease processes such as dissections, aneurysms, and penetrating ulcers.

Open surgical repair procedures have traditionally been used to address those disease processes. Many open surgical repair procedures are invasive and are accompanied by high rates of morbidity and mortality. More recently, endovascular techniques have been proposed and used in place of open surgical repair procedures.

SUMMARY

According to one aspect of the disclosure, a prosthetic endograft device is disclosed. The device includes a first component including an outer diameter equal to a first diameter, a second component attached to a distal end of the first component, and a plurality of third components positioned in a chamber defined in the second component. The second component includes a proximal surface extending outwardly from the distal end of the first component, and a plurality of openings defined in the proximal surface. Each third component includes a passageway extending inwardly from an opening of the plurality of openings defined in the proximal surface. Each passageway is sized to receive a tubular conduit, and the proximal surface has an outer edge that defines a second diameter greater than the first diameter.

In some embodiments, the second component may include an inner distal surface positioned opposite the proximal surface and an inner side surface extending distally from the inner distal surface. Each third component may include a body having a first end secured to the inner distal surface and a side wall removably coupled to the inner side surface of the second component.

In some embodiments, the device may include a plurality of fasteners configured to removably couple the third components to the inner side surface of the second component. Each fastener may be moveable between a first position in which the side wall of the body is attached to the inner side surface, and a second position in which the side wall is detached from the inner side surface such that a second end of the body is permitted to move within the chamber of the second component.

In some embodiments, the second component may include a plurality of first rings secured to the inner side surface. Each third component may include a plurality of second rings secured to the side wall of the body, and each fastener may include a trigger wire extending through the first rings and the second rings when the fastener is in the first position.

In some embodiments, the second component may include an outer surface extending from a proximal end connected to the outer edge of the proximal surface to a distal end. The outer surface may be positioned opposite the inner side surface of the second component.

In some embodiments, the outer surface of the second component may have a frustoconical shape such that the distal end has an outer diameter less than the second diameter. In some embodiments, the outer surface may be a first outer surface of the second component and the second component includes a second outer surface extending from the first outer surface to the distal end of the second component. The second outer surface may be substantially cylindrical.

In some embodiments, the outer surface of the second component may be substantially cylindrical. In some embodiments, the proximal surface of the second component may have a frustoconical shape.

In some embodiments, the passageway of each third component may extend inwardly from the first end to a second end. Each passageway may have a first inner diameter at the first end and a second inner diameter at the second end that is less than the first inner diameter.

In some embodiments, the first component may include a distal section including the distal end of the first component. The distal section may have an outer diameter equal to the first diameter. The first component may also include a proximal section attached to the distal section. The proximal section may have an outer diameter equal to a third diameter greater than the first diameter.

In some embodiments, the proximal section may be expandable between a first position in which the outer diameter of the proximal section is equal to the first diameter, and a second position in which the outer diameter of the proximal section is equal to the third diameter. Additionally, in some embodiments, the prosthetic endograft device may include a restraint configured to prevent the proximal section from expanding.

Additionally, in some embodiments, each third component of the plurality of third components may include a first metallic stent and a second metallic stent coupled to the first metallic stent. The second metallic stent may be formed from a pair of wires wrapped in a double helix.

In some embodiments, the device may include an outer mesh cage having a first end secured to the first component and a second end secured to the second component. The outer mesh cage may include at least one opening sized to receive the tubular conduit and a cavity in which the proximal surface of the second component is positioned.

In some embodiments, the device may include a first radiopaque marker attached to a proximal end of the first component, a second radiopaque marker attached to a distal end of the second component, and a plurality of third radiopaque markers. Each third radiopaque marker may be associated with each third component.

According to another aspect, a prosthetic device includes a first component including a first cylindrical outer surface having a first diameter, and a second cylindrical outer surface having a second diameter less than the first diameter. The device also includes a second component attached to a distal end of the first component. The second component includes a proximal surface extending outwardly from the distal end of the first component, and a plurality of openings defined in the proximal surface. The device further includes a plurality of third components positioned in a chamber defined in the second component. Each third component includes a passageway aligned with an opening of the plurality of openings defined in the proximal surface. Each passageway is sized to receive a tubular conduit, and the proximal surface has an outer edge that defines a third diameter greater than the second diameter.

In some embodiments, when the prosthetic endograft device is viewed in a first plane, an angle may be defined between the proximal surface of the second component and the second cylindrical outer surface. The angle may have a magnitude of greater than or equal to 90 degrees.

In some embodiments, the magnitude of the angle may be equal to approximately 150 degrees.

In some embodiments, the passageway of each third component may extend inwardly from a first end positioned over the opening to a second end. Each passageway may have a first inner diameter at the first end and a second inner diameter at the second end that is less than the first inner diameter.

According to another aspect, a method of repairing a patient's aorta is disclosed. The method includes positioning a prosthetic endograft device in an aortic arch of the patient's aorta, aligning an opening defined in the prosthetic endograft device with a subclavian artery, advancing a tubular conduit proximally through the opening of the prosthetic endograft device, and positioning an end of the tubular conduit in the subclavian artery.

One general aspect includes a vascular prosthetic graft device including: a first component. The vascular prosthetic graft device also includes a second component, where the second component is engaged with the first component and defines a radially outwardly extending shoulder that extends outwardly of a major diameter of one of the first component or the second component. The vascular prosthetic graft device also includes at least one of the first and second components is supported by wire frame material. The vascular prosthetic graft device also includes at least one opening defined on the shoulder for receiving one end of a stent member. The vascular prosthetic graft device also includes where the other end of the stent member is received within one of the aortic branch vessels.

Implementations may include one or more of the following features. The graft device includes a first component and a second component. The first component and the second component each have a major diameter that is about equal to the major diameter of the other component. The first component and the second component may be covered with a graft material. Each opening may extend into the second component at an angle relative to a horizontal defined through the second component. The shoulder may extend radially a distance from a horizontal defined through the second component to a position aligned with a major diameter of one portion of the first component. The first component may define a portion recessed relative to the second component for providing clearance for insertion of the stent member. A guide wire may extend through the opening, where the guide wire is inserted through a selected one of the aortic branch vessels, where the guide wire is engaged with the stent member, where the guide wire is translated through the selected artery until the stent member is proximal a deployed position. The stent member may be released to expand the member into engagement with the selected aortic branch vessels. The graft device may include a cage positioned at least partially around the opening for maintaining the opening apart from a wall of the aorta to provide clearance for insertion of the stent member. The shoulder extends perpendicularly relative to a horizontal defined through the second component. The shoulder may extend at a non-orthogonal angle relative to a horizont6+al defined through the second component. The graft device is slidably engaged with a stent device extending through the ascending aorta to define a total length of the engaged graft device and stent device. The graft device spans from a position that extends from the ascending aorta to the descending aorta. The graft device spans from a position that extends from the descending aorta to the abdominal aorta. The graft device receives a tubular conduit to which the one end of the stent member is received. A trigger wire is engaged with an outer surface of a tubular conduit attaching the tubular conduit to an inner surface of the second component using suture eyelets, where manipulation of the trigger wire allows the separation of a distal portion of the tubular conduit from the second component changing an angle of entry of the stent member. The graft device may include a first radiopaque marker attached to a proximal end of the first component and second radiopaque marker attached to a distal end of the second component. The graft device may include a plurality of third radiopaque markers defined on openings on the shoulder of the second component. The first component and the second component each have a major diameter that is about equal to the major diameter of the other component. In one or more embodiments, the first component and the second component are covered with a graft material. Each opening extends into the second component at an angle relative to a horizontal defined through the second component. In one or more embodiments, the shoulder extends radially a distance from a horizontal defined through the second component to a position aligned with a major diameter of one portion of the first component. In one or more embodiments, the first component defines a portion recessed relative to the second component for providing clearance for insertion of the stent member. In one or more embodiments, the method may include inserting a guidewire through a selected one of the aortic branch vessels, where the guidewire is engaged with the stent member, where the guidewire is translated through the selected artery until the stent member is proximal a deployed position. In one or more embodiments, the stent member is released to expand the member into engagement with the selected aortic branch vessels. In one or more embodiments, the method may include positioning a cage at least partially around the opening for maintaining the opening apart from a wall of the aorta to provide clearance for insertion of the stent member. In one or more embodiments, the shoulder extends perpendicularly relative to a horizontal defined through the second component. In one or more embodiments, the shoulder extends at a non-orthogonal angle relative to a horizontal defined through the second component. In one or more embodiments, the graft device is slidably engaged with a stent device extending through the ascending aorta to define a total length of the engaged graft device and stent device. In one or more embodiments, the graft device spans from a position that extends from the ascending aorta to the descending aorta. In one or more embodiments, the graft device spans from a position that extends from the descending aorta to the abdominal aorta. In one or more embodiments, the opening receives a tubular conduit to which the one end of the stent member is received. In one or more embodiments, a trigger wire is engaged with an outer surface of a tubular conduit attaching the tubular conduit to an inner surface of the second component using suture eyelets, the method further including manipulating the trigger wire to allow separation of a distal portion of the tubular conduit from the second component changing an angle of entry of the stent member. In one or more embodiments, the device includes a first radiopaque marker attached to a proximal end of the first component and second radiopaque marker attached to a distal end of the second component. In one or more embodiments, the device further includes a plurality of third radiopaque markers defined on openings on the shoulder of the second component. In one or more embodiments, the method may include aligning an opening includes rotation of the device into a desired orientation.

BRIEF DESCRIPTION OF THE DRAWINGS

Embodiments of the present disclosure will now be described by way of example in greater detail with reference to the attached figures, in which:

FIG. 1 is a side elevation view of one embodiment of a branched aortic graft device;

FIG. 2 is a view similar to FIG. 1 showing the branched aortic graft device in a deployed configuration;

FIG. 9 is a side elevation view of another embodiment of a branched aortic graft device;

FIG. 10 is a view similar to FIG. 9 showing the branched aortic graft device in a deployed configuration;

DETAILED DESCRIPTION OF THE DRAWINGS

Figure 3:
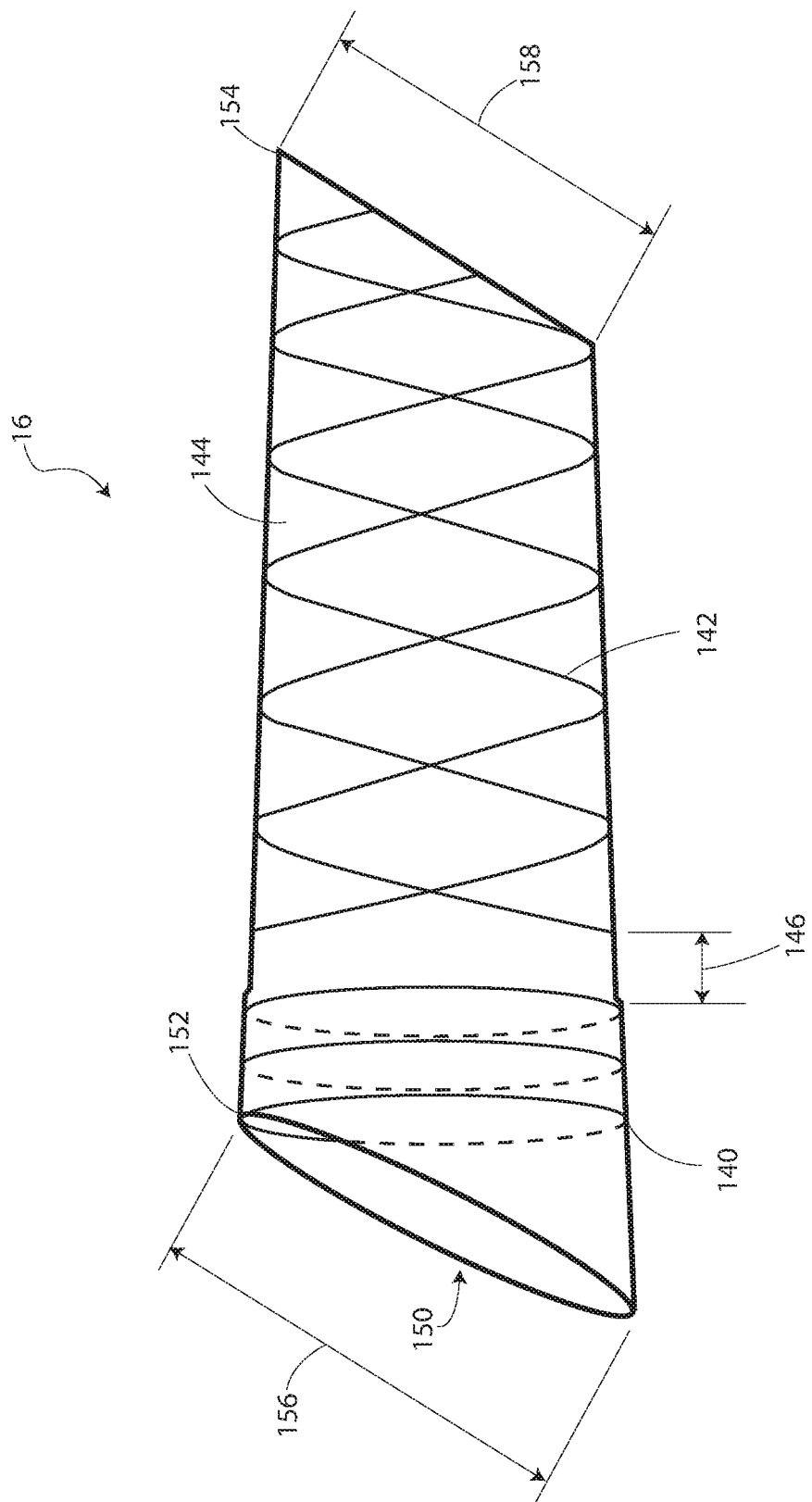
FIG. 3 is a side perspective view of a branch component of the branched aortic graft device of FIG. 1.

While the concepts of the present disclosure are susceptible to various modifications and alternative forms, specific exemplary embodiments thereof have been illustrated by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, distal, proximal, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise. For example, the term "proximal" refers to the direction that is generally closest to the heart, and the term "distal" refers to the direction that is generally furthest from the heart.

Referring now to FIG. 1, a prosthetic endograft device 10 (hereinafter device 10) is shown. The device 10 is configured to be positioned in an arch of a patient's aorta. The device 10 includes a proximal component 12, a distal component 14, and a plurality of branch components 16 attached to the distal component 14. As described in greater detail below, each branch component 16, is sized to support a tubular conduit 18 (see FIG. 8) that may be advanced into the visceral branches or the braches of the arch of the patient's aorta.

The proximal component 12 of the device 10 is configured to be positioned in a patient's ascending aorta and extend into the aortic arch. The component 12 includes a frame 20 constructed from self-expanding stainless steel. It should be appreciated that in other embodiments the frame 20 may be formed from nitinol or other metal alloy. The frame 20 is covered by a layer 22 formed from polyester. In other embodiments, the layer 22 may be formed from ePTFE or other biologically inert material impermeable to blood or serum.

As shown in FIGS. 1-2, the component 12 has a proximal end 24, which is also the proximal end of the device 10, and a distal end 26 attached to the distal component 14. The component 12 includes a proximal section 28 that extends from the end 24 to connect to a distal section 30 at a seam 32. The distal section 30 extends from the seam 32 to the end 26. It should be appreciated that the proximal section 28 and the distal section 30 may be formed as a single piece such that the seam is omitted. In the illustrative embodiment, the distal section 30 has a cylindrical outer surface 34, which has a diameter 36 equal to approximately 24 millimeters. It should be appreciated that in other embodiments the diameter 36 may vary based on, for example, the size of the patient's aorta. As used herein, major diameter may refer to any diameter of a major portion of a component.

The proximal section 28 of the component 12 includes a main body 40 and a connecting body 42 that connects the main body 40 to the distal section 30. In the illustrative embodiment, the proximal section 28 is expandable between a compressed position shown in FIG. 1 and an expanded position shown in FIG. 2. In the compressed position, the outer surface 44 of the main body 40 and the outer surface 46 of the connecting body 42 define a cylindrical shape. As shown in FIG. 1, the surfaces 44, 46 of the proximal section 28 have the same diameter 36 as the distal section 30 when in the compressed position, thereby facilitating access to the aortic arch branches and uninterrupted blood flow through aorta when the device 10 is initially positioned in the aortic arch.

When the proximal section 28 is expanded as shown in FIG. 2, the outer surface 44 of the main body 40 continues to have a cylindrical shape but has a diameter 48 greater than the diameter 36 of the distal section 30. In the illustrative embodiment, the diameter 48 is equal to approximately 38 millimeters. In the expanded position, the outer surface 46 of connecting body 42 defines a frustoconical shape that tapers from the diameter 48 to the diameter 36.

The component 12 includes a restraint 50 that maintains the proximal section 28 in the compressed position prior to surgery. In the illustrative embodiment, the restraint 50 includes a plurality of circumferential diameter reducing ties 52, 54, 56 and a trigger wire 58. Each tie is formed from Prolene or other monofilament suture material and includes loops 62, 64 formed at each end. The ties 52, 54, 56 extend around the outer surfaces 44, 46 of the bodies 40, 42, respectively, such that the loops 62, 64 are aligned. The trigger wire 58 is positioned in the loops 62, 64 of the ties 52, 54, 56 to maintain tension on the ties 52, 54, 56. To expand the proximal section 28, the trigger wire 58 is withdrawn from the loops 62, 64 of the ties 52, 54, 56, thereby releasing the ties 52, 54, 56. When released, the self-expanding frame 20 of the main body 40 expands to outward to the position shown in FIG. 2. It should be appreciated that in other embodiments the proximal section 28 may have a single, fixed configuration such that a restraint may be omitted.

The proximal component 12 has a length 66 defined between the proximal end 24 and the distal end 26. In the illustrative embodiment, the length 66 is equal to approximately 95 millimeters. The main body 40 of the proximal section 28 also has a length 68, which is approximately 50 millimeters in the illustrative embodiment. As described in greater detail below, the proximal component 12 also has a tubular chamber 70 defined therein, which extends between openings defined in the proximal end 24 and the distal end 26, and connects to a tubular chamber 72 defined in the distal component 14 to form a common passageway 74 extending through the device 10.

As described above, the distal component 14 of the device 10 is connected to the distal end 26 of the proximal component 12. The proximal component 12 of the device 10 is configured to be positioned into a patient's ascending aorta and extend into the aortic arch. The component 14 includes a frame 80 constructed from self-expanding stainless steel. It should be appreciated that in other embodiments the frame 80 may be formed from nitinol or other metal alloy. The frame 80 is covered by a layer 82 formed from polyester. In other embodiments, the layer 82 may be formed from ePTFE or other biologically inert material impermeable to blood or serum.

As shown in FIG. 1, the distal component 14 has a proximal end 84, which is attached to the distal end 26 of the proximal component 12, and a distal end 86, which is also the distal end of the device 10. The component 14 includes a proximal section 88 that extends from the end 84 to connect to a distal section 90. The distal section 90 extends to the end 86. In the illustrative embodiment, the distal section 90 has a cylindrical outer surface 94, which has a diameter 96 equal to approximately 24 millimeters. It should be appreciated that in other embodiments the diameter 96 may vary based on, for example, the size of the patient's aorta.

The proximal section 88 of the component 14 includes a proximal surface 100 that extends outwardly from the cylindrical outer surface 34 of the component 12. As shown in FIG. 1, the proximal surface 100 extends to an outer edge 102, and the proximal section 88 includes an outer surface 104 connects the outer edge 102 to the cylindrical outer surface 94 of the distal section 90. Collectively, these components define a shoulder that extends from one diameter of component 14. In the illustrative embodiment, the outer edge 102 of the proximal surface 100 has a diameter 106 that is greater than the diameter 36 of the component 12. In the illustrative embodiment, the diameter 106 is equal to approximately 34 millimeters.

When the proximal section 28 of the component 12 is expanded as shown in FIG. 2, the connecting body 42 of the proximal section 28, the distal section 30, and the proximal surface 100 of the component 14 cooperate to define an annular compartment 110. The annular compartment 110 need not extend circumferentially along the entirety of the distal section 30, and may only partially extend. As described in greater detail below, the annular compartment 110 provides a surgeon or other operator with a working space when the device 10 is positioned in a patient's aorta and facilitates access to the aortic arch branches during a procedure.

As shown in FIGS. 1-2, the proximal surface 100 of the component 14 has a frustoconical shape that tapers from the diameter 36 to the diameter 106. When the device 10 is viewed as shown in FIG. 1, an angle 112 is defined between the proximal surface 100 and the cylindrical outer surface 34 of the component 12. In the illustrative embodiment, the angle 112 is equal to approximately 150 degrees. In other embodiments, the angle 112 may be greater than or equal to 90 degrees. In one particular embodiment, the angle 112 may be equal to 153.4 degrees. In another embodiment, the angle 112 may be equal to 135 degrees.

The outer surface 104 of the component 14 extending from the outer edge 102 of the proximal surface 100 also has a frustoconical shape that tapers from the diameter 106 to the diameter 96 of the cylindrical outer surface 94 of the distal section 90. It should be appreciated that in other embodiments the outer surface 104 may be cylindrical and may have the same diameter as the cylindrical outer surface 94 of the distal section 90.

The distal component 14 has a length 114 defined between the proximal end 84 and the distal end 86. In the illustrative embodiment, the length 114 is equal to approximately 110 millimeters. It should be appreciated that in other embodiments the length 114 may be between 100 millimeters and 150 millimeters. The proximal surface 100 has a length 116, which is equal to approximately 10 millimeters in the illustrative embodiment, and the outer surface 104 has a length 118, which is equal to approximately 30 millimeters in the illustrative embodiment. The distal component 14 has a tubular chamber 72 defined therein, which connects with the tubular chamber 70 of the proximal component 12 to form a common passageway 74 extending through the device 10.

As shown in FIGS. 1-2, the proximal surface 100 of the component 14 has a plurality of openings 120 defined therein, though only one opening could be employed in certain embodiments. The openings 120 are radially spaced apart from each other. In the illustrative embodiment, each opening 120 is spaced apart from the next opening by 90 degrees. The component 14 includes three openings 120 in the illustrative embodiment, but, in other embodiments, the component 14 may include additional or fewer openings.

Each opening 120 in the proximal surface 100 is sized to receive a tubular conduit 18. As shown in FIG. 1, each opening 120 has a diameter 122. In the illustrative embodiment, the diameter 122 is equal to approximately 10 millimeters. As described in greater detail below, the plurality of branch components 16 of the device 10 are aligned with the openings 120 defined in the proximal surface 100.

The device 10 includes a plurality of radiopaque markers 124, which are secured to the proximal component 12 and the distal component 14. Each radiopaque marker 124 is illustratively embodied as a thin-walled metal tube or inclusion body that is visible under x-ray fluoroscopy. Each marker 124 may be formed from a high density metal such as, for example, platinum, gold, or tantalum. In the illustrative embodiment, radiopaque markers 124 are secured to the proximal end 24 of the proximal component 12 (i.e., the proximal end of the device 10) and to the distal end 86 of the distal component 14 (i.e., the distal end of the device 10). Additional radiopaque markers 126 are associated with each opening 120 defined in the distal component 14 to identify the locations of the branch components 16. Other radiopaque markers 128 may be used to identify the location of the outer edge 102 of the distal component 14.

As described above, the device 10 includes a plurality of branch components 16 attached to the distal component 14. One embodiment of a branch component 16 is shown in FIG. 3. The branch component 16 includes a proximal frame 140 and a distal frame 142 that is connected to the distal frame 142. The proximal frame 140 is formed by looping memory shape metallic wire. As shown in FIG. 3, the two proximal-most loops are angled to each other.

The distal frame 142 is also formed from memory shape metallic wire that is wrapped in a double-helix form. It should be appreciated that in other embodiments a triple- or quadruple-helix arrangement may be used. In other embodiments, the frames 140, 142 may also be formed from as self-expanding frames from stainless steel or nitinol, z-stents, or other metallic tubular components. The branch component 16 has a layer 144 formed from polyester or ePTFE. In the illustrative embodiment, the outer layer 144 couples the proximal frame 140 to the distal frame 142. A gap 146 is defined between the frames 140, 142, which permits flexibility between the frames 140, 142. In the illustrative embodiment, the gap 146 is equal to approximately 2 millimeters.

The frames 140, 142 cooperate to define a passageway 150 sized to receive a tubular conduit 18. The passageway 150 extends from a proximal end 152 of the branch component 16 to a distal end 154. As shown in FIG. 3, the passageway 150 is tapered and has an inner diameter 156 at the proximal end 152 that is greater than an inner diameter 158 at the distal end 154. In the illustrative embodiment, the inner diameter 156 is equal to approximately 10 to 12 millimeters, while the inner diameter 158 is equal to approximately 8 millimeters. In the illustrative embodiment, the double-helix form of the distal frame 142 permits the post-dilation of the passageway 150 to a larger diameter as needed.

Figure 4:
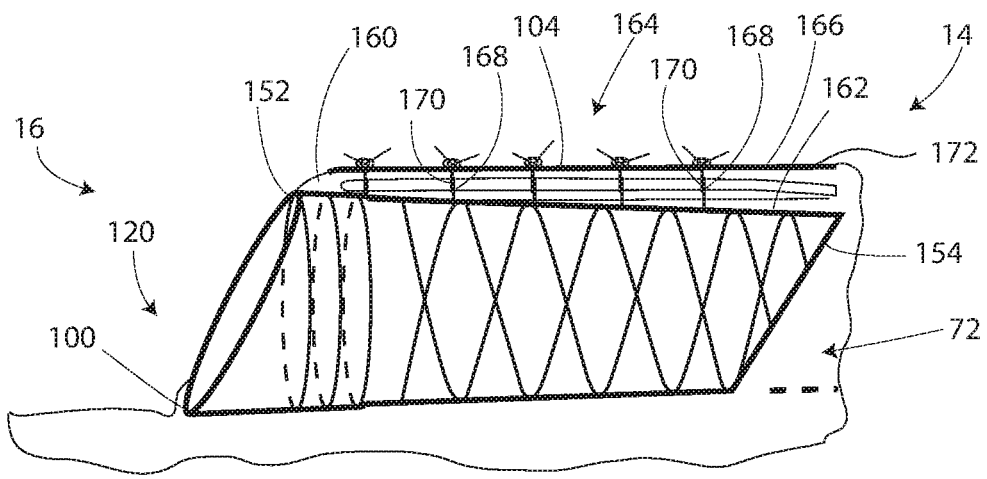
FIG. 4 is a fragmentary view of the branch component of FIG. 3 in a storage position.
Figure 5:
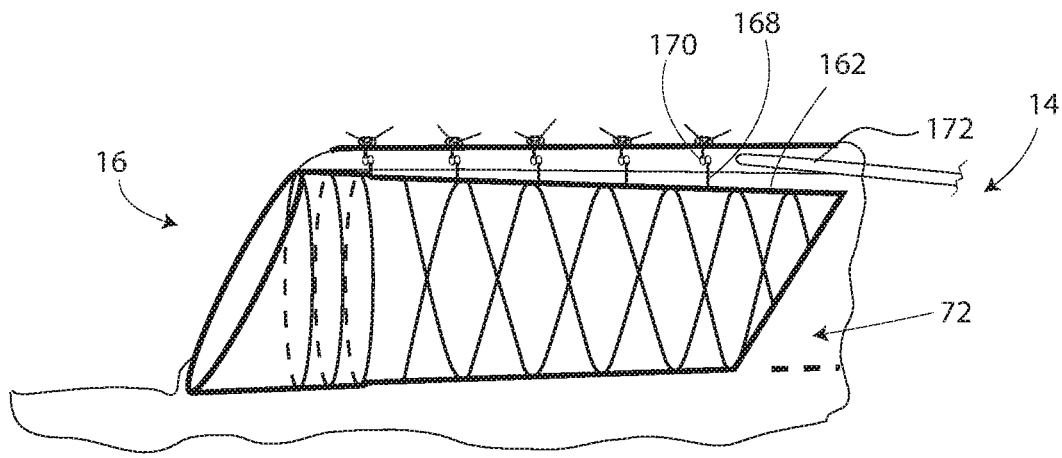
FIG. 5 is a view similar to FIG. 4 of the branch component released from the storage position.
Figure 6:
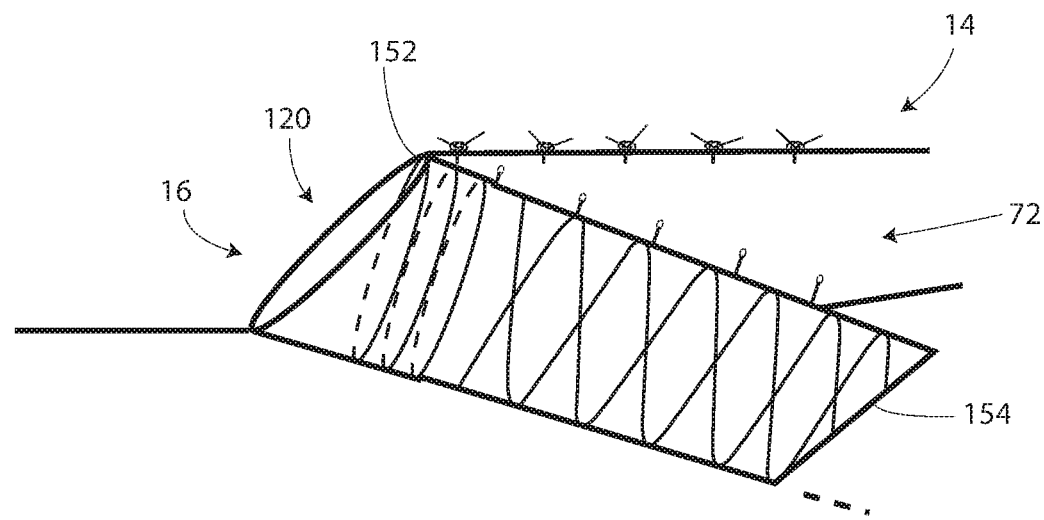
FIG. 6 is a view similar to FIGS. 4-5 showing the branch component in a deployed position.

As shown in FIGS. 4-6, each branch component 16 is positioned in the chamber 72 of the distal component 14 such that the passageway 150 is aligned with and covers one of the openings 120 defined in the distal component 14. As shown in FIG. 4, the proximal end 152 of the branch component 16 is secured an inner surface 160 of the distal component 14 opposite the proximal surface 100. In the illustrative embodiment, the branch component 16 is sewn onto the inner surface 160. It should be appreciated that in other embodiments other fasteners may be used to secure the proximal end 152 of the branch component 16 to the distal component 14.

The branch component 16 also has an outer side wall 162 that is removably coupled to the distal component 14 via a fastener 164. As shown in FIG. 4, the outer side wall 162 is positioned adjacent an inner side surface 166 of the distal component 14. In the illustrative embodiment, the fastener 164 includes a plurality of loops 168 extending from the side wall 162 and a corresponding plurality of loops 170 extending from the inner side surface 166 of the distal component 14. A trigger wire 172 extends through the loops 168, 170 to secure the outer side wall 162 of the branch component 16 to the distal component 14. When the trigger wire 172 is removed from the loops 168, 170 as shown in FIG. 5, the outer side wall 162 of the branch component 16 is released, thereby permitting the distal end 154 of the branch component 16 to float freely in the chamber 72 of the distal component 14. In that way, the branch component 16 may conform to a relaxed position to avoid angles that would kink the tubular conduit 18.

Figure 7:
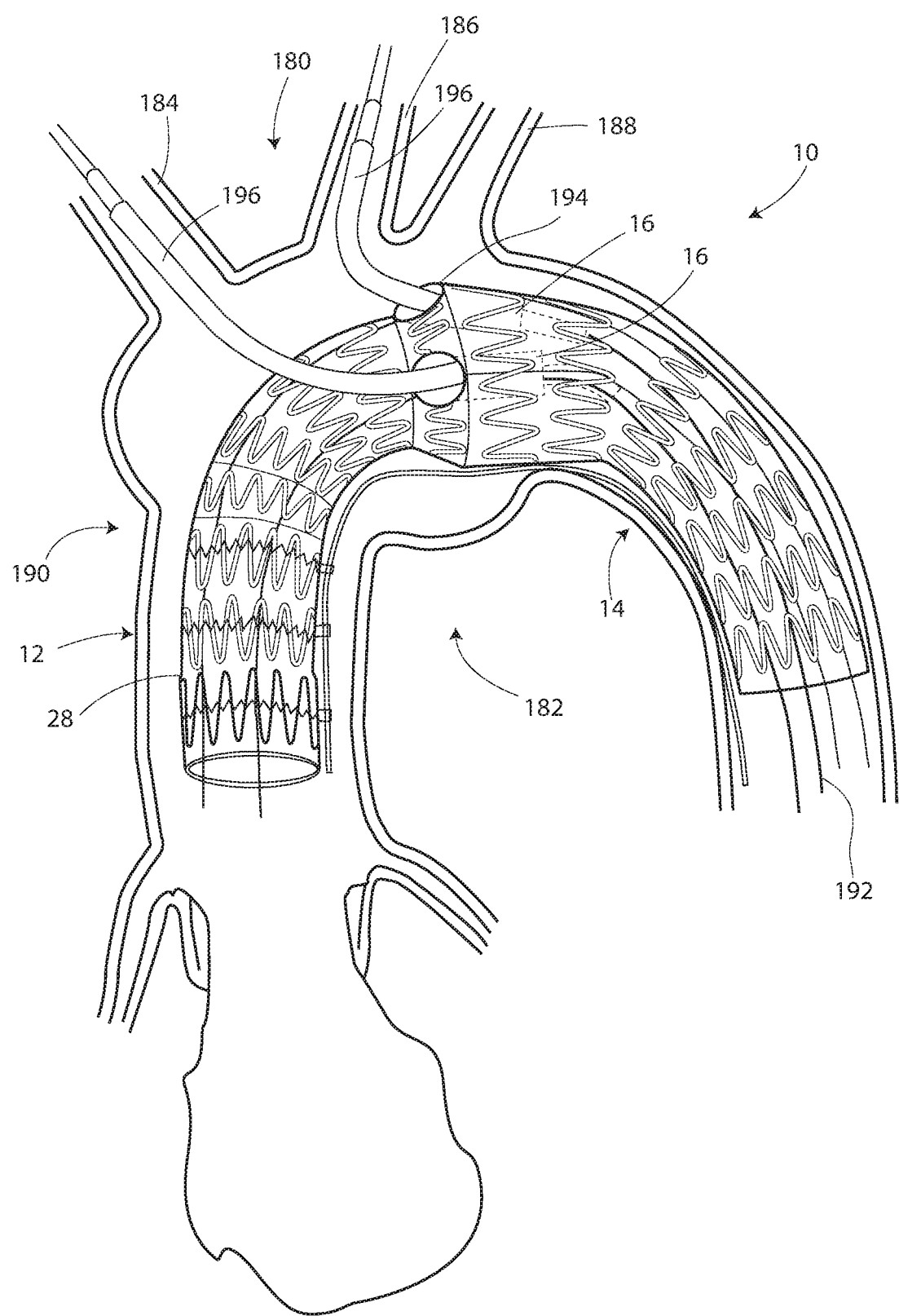
FIG. 7 is a view of the branched aortic graft device of FIG. 1 positioned in an aortic arch.
Figures 8, 8A:
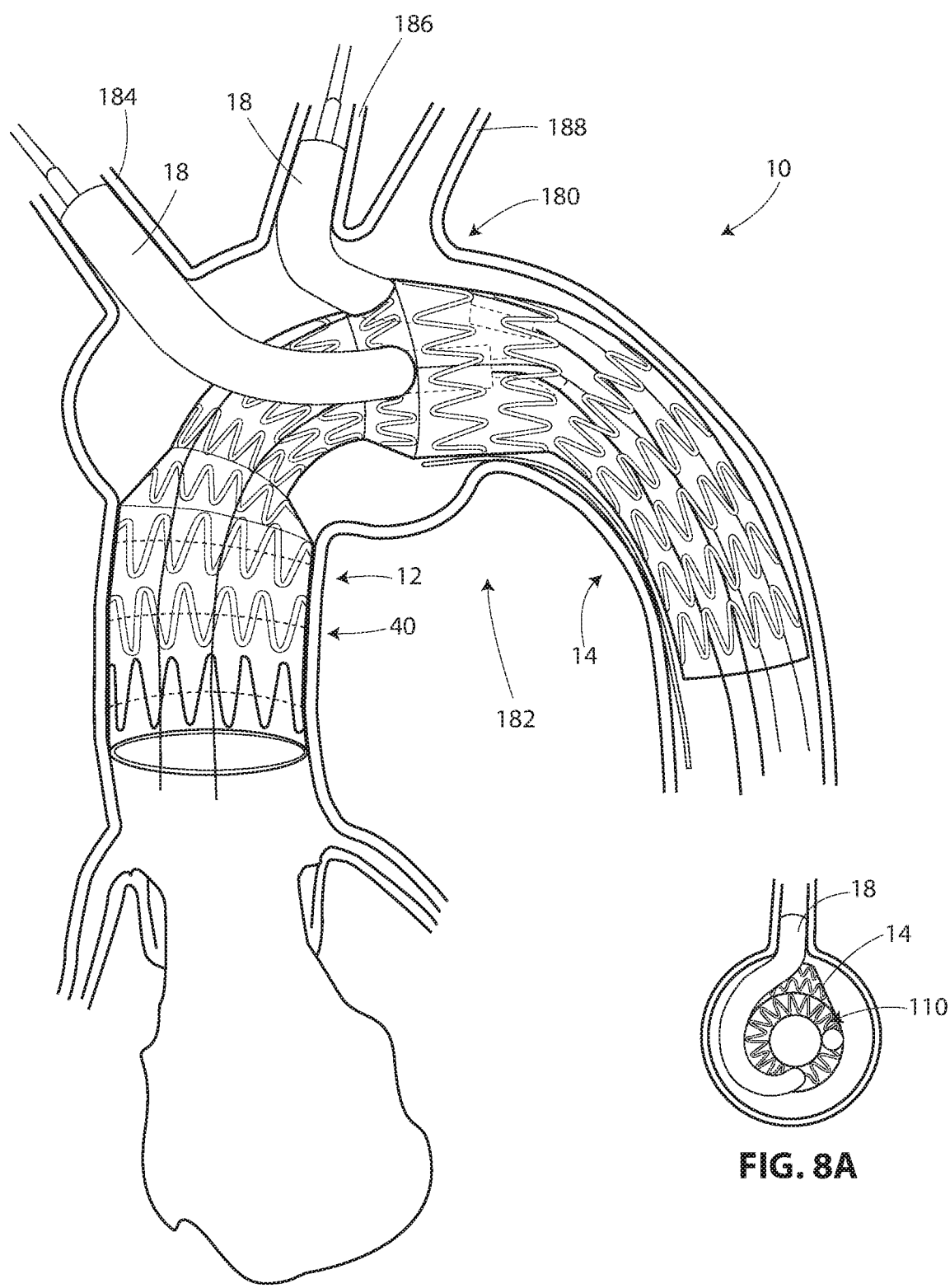
FIG. 8 is a view similar to FIG. 7 showing the branched aortic graft device in a deployed position.
FIG. 8A is a cross sectional view taken along the line A-A in FIG. 8.

As described above, the device 10 may be used in an arch 180 of a patient's aorta 182, as shown in FIGS. 7-8. Prior to insertion of the device 10, exposure to the common femoral artery (not shown) and the common carotid arteries 184, 186 is performed. A left carotid-subclavian bypass may then be performed. Alternatively, the left subclavian artery 188 is exposed and prepared to receive a tubular stent 18 from the device 10. After the patient is heparinized, a medium stiff wire 192 is placed into the ascending aorta 190. The device 10, which is encased in an outer sheath (not shown) of a delivery system, may be advanced over the wire 192 into the arch 180.

The surgeon or other operator may perform an aortogram to identify the positions of the aortic arch branches for appropriate positioning of components 16 in the arch 180. In the illustrative embodiment, the openings 120 in the distal component 14 are marked with double radio-opaque markers 194 to facilitate radiographic identification of the branch components 16. After performing an aortogram, one of the double radiopaque markers 194 of the device 10 is aligned with opening of the subclavian artery 188. When the device 10 is properly aligned, the device 10 may be initially deployed by unsheathing the outer sheath of the delivery system. As shown in FIG. 7, the proximal section 28 of the proximal component 12 remains in the compressed position when the device 10 is initially deployed.

Each branch component 16 is precannulated with a wire 196 passing through the delivery system. After the carotid arteries 184, 186 have been exposed and cannulated using standard sheaths, the wire 196 may be snared by inserting a snare through the sheath positioned in the carotid artery 184 and inserting another snare through the sheath positioned in the carotid artery 186. Utilizing each snare separately, each wire 196 may be grasped and pulled through the sheath in the corresponding carotid artery to establish the femoro-carotid through wire. Once the femoro-carotid through wire is established, a 4 Fr or 5 Fr catheter may be tracked over this wire from the femoral artery to each of the carotid arteries 184, 186 and out through the corresponding sheath.

The wire 196 may be removed and exchanged for a standard stiff wire on both sides to cannulate two of the branch components 16. In other embodiments, the branch components 16 may be cannulated with guide catheters or wires from sheaths previously placed in the common carotid arteries 184, 186. These stiff wires will be used to track the tubular stents 18 into the branch components 16. The proximal section 28 may then be expanded to fully deploy the device 10.

To do so, the trigger wire 58 of the restraint 50 is withdrawn from the loops 62, 64 of the reducing ties 52, 54, 56. When released, the self-expanding frame 20 of the main body 40 of the component 12 expands to outward to the position shown in FIG. 8. In the expanded position, the main body 40 engages the walls of the ascending aorta 190.

One or more tubular stents 18 may advanced through the branch components 16 over the wires 196 and into the carotid arteries 184, 186. When carotid circulation has been confirmed and the wires 196 removed, the outer side wall 162 of each branch component 16 may be released from the inner side surface 166 of the distal component 14. To do so, the trigger wire 172 is withdrawn from the loops 168, 170 of the fastener 164. When the trigger wire 172 is removed, the distal end 154 of the branch component 16 is permitted to float freely in the chamber 72 of the distal component 14. In that way, the branch component 16 may conform to a relaxed position to avoid angles that would kink the tubular conduit 18. As shown in FIG. 8A, the configuration of the annular compartment 110 defines a space in which the tubular stents 18 are permitted to bend and flex to gain access to the arteries 184, 186.

Figure 11:
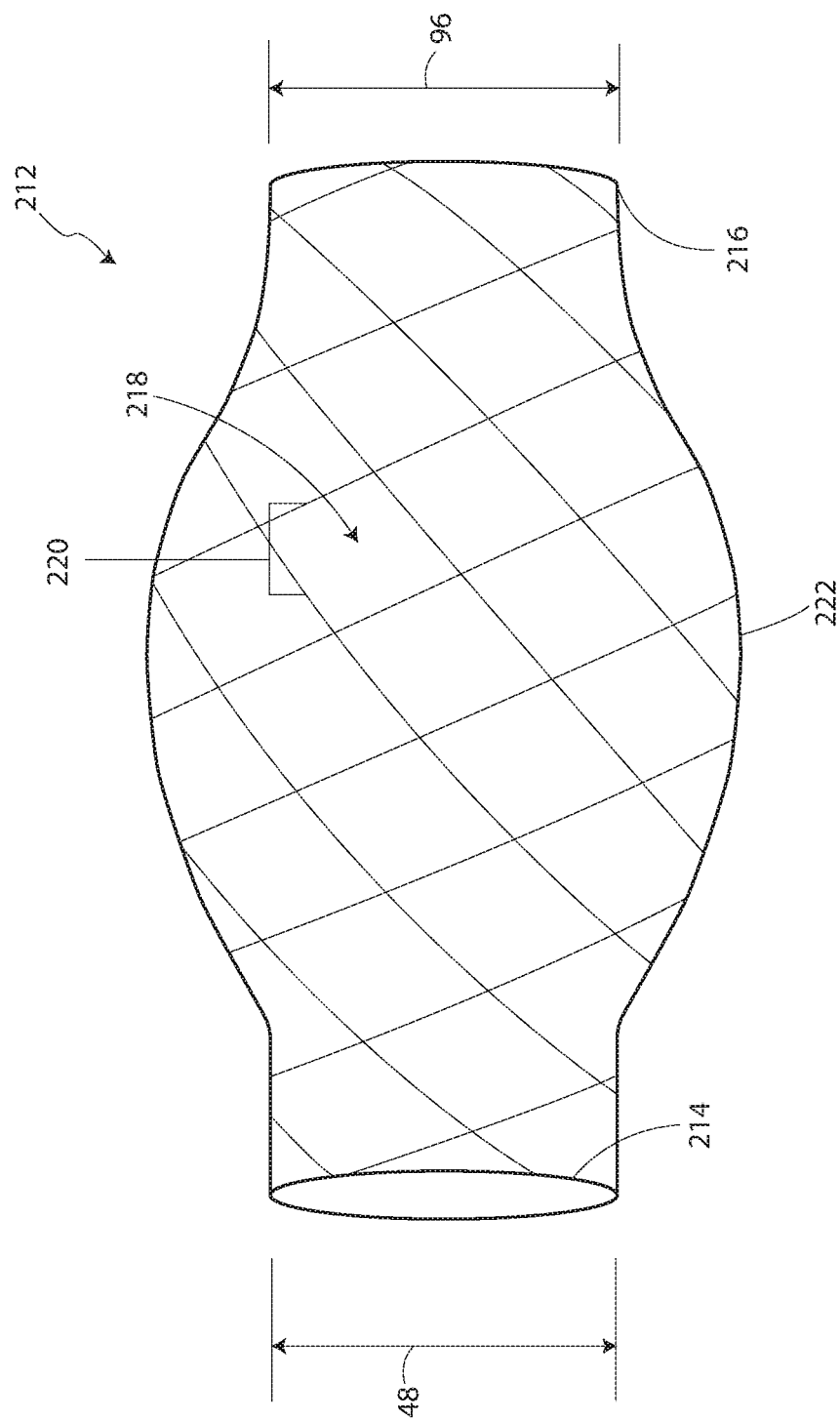
FIG. 11 is side perspective view of a cage of the branched aortic graft device of FIGS. 9-10.

Referring now to FIGS. 9-11, another embodiment of prosthetic endograft device (hereinafter device 210) is shown. The embodiment of FIGS. 9-11 includes a number of features that are the same or substantially the same as those described above in regard to the embodiment of FIGS. 1-8. Such features are identified in FIGS. 9-11 with the same reference numbers used in FIGS. 1-8. The device 210 includes a proximal component 12, a distal component 14, and a plurality of branch components 16 attached to the distal component 14. As shown in FIG. 9, the device 210 also includes a mesh cage 212, which is configured to enclose the annular compartment 110 of the device 210 when the device 210 is deployed in the patient's aorta.

The mesh cage 212 includes a proximal end 214 secured to the connecting body 42 of the proximal component 12 and a distal end 216 secured to the outer surface 104 of the distal component 14. The cage 212 has an open-cell structure that includes a plurality of openings 218 sized to permit the passage of the tubular conduits 18. As shown in FIG. 11, each opening 218 has a diameter 220. In the illustrative embodiment, each diameter 220 is between 8 to 10 millimeters in diameter.

As shown in FIGS. 9-10, the mesh cage 212 is moveable between a compressed position and an expanded position. In the illustrative embodiment, the mesh cage 212 is in the compressed position shown in FIG. 9 when the proximal component 12 is compressed. When the proximal component 12 is expanded as shown in FIG. 10, the proximal end 214 moves outward with the connecting body 42 to the expanded position.

In the expanded position, the mesh cage 212 increases in diameter between the proximal end 214 and a mid-section 222. The mesh cage 212 decreases in diameter between the mid-section 222 and the distal end 216. In that way, the proximal end 214 of the mesh cage 212 has the diameter 48 (i.e., the same diameter as the main body 40) and the distal end 216 has the diameter 96 (i.e., the same diameter as the distal section 90 of the component 14.

As described above, the mesh cage 212 encloses the annular compartment 110 of the device 210. A cavity 224 is defined within the mesh cage 212, and, as shown in FIG. 10, the cavity 224 includes the annular compartment 110. When the device 210 is deployed in the patient's aorta, the mesh cage 212 spaces the openings 120 of the distal component 14 apart from the walls of the aortic arch, thereby providing a work space for the surgeon.

Figure 12:
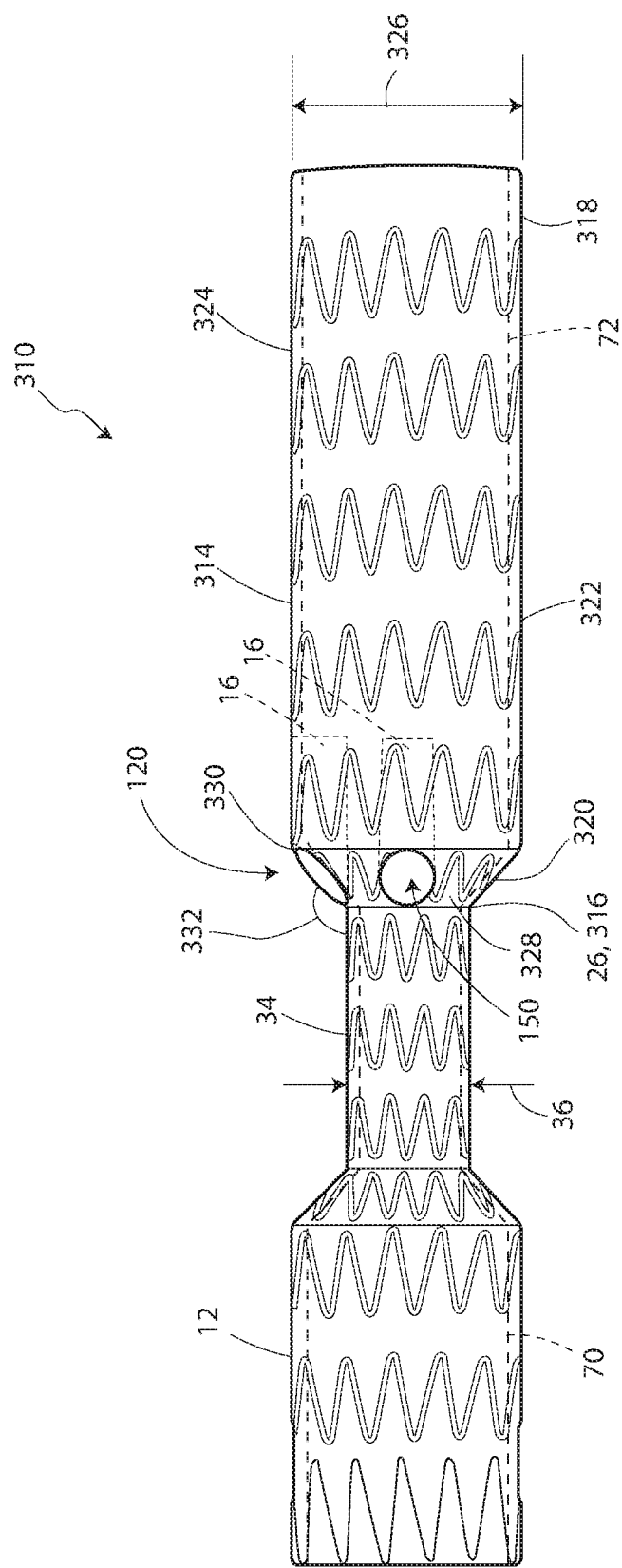
FIG. 12 a side elevation view of another embodiment of a branched aortic graft device.
Figure 13:
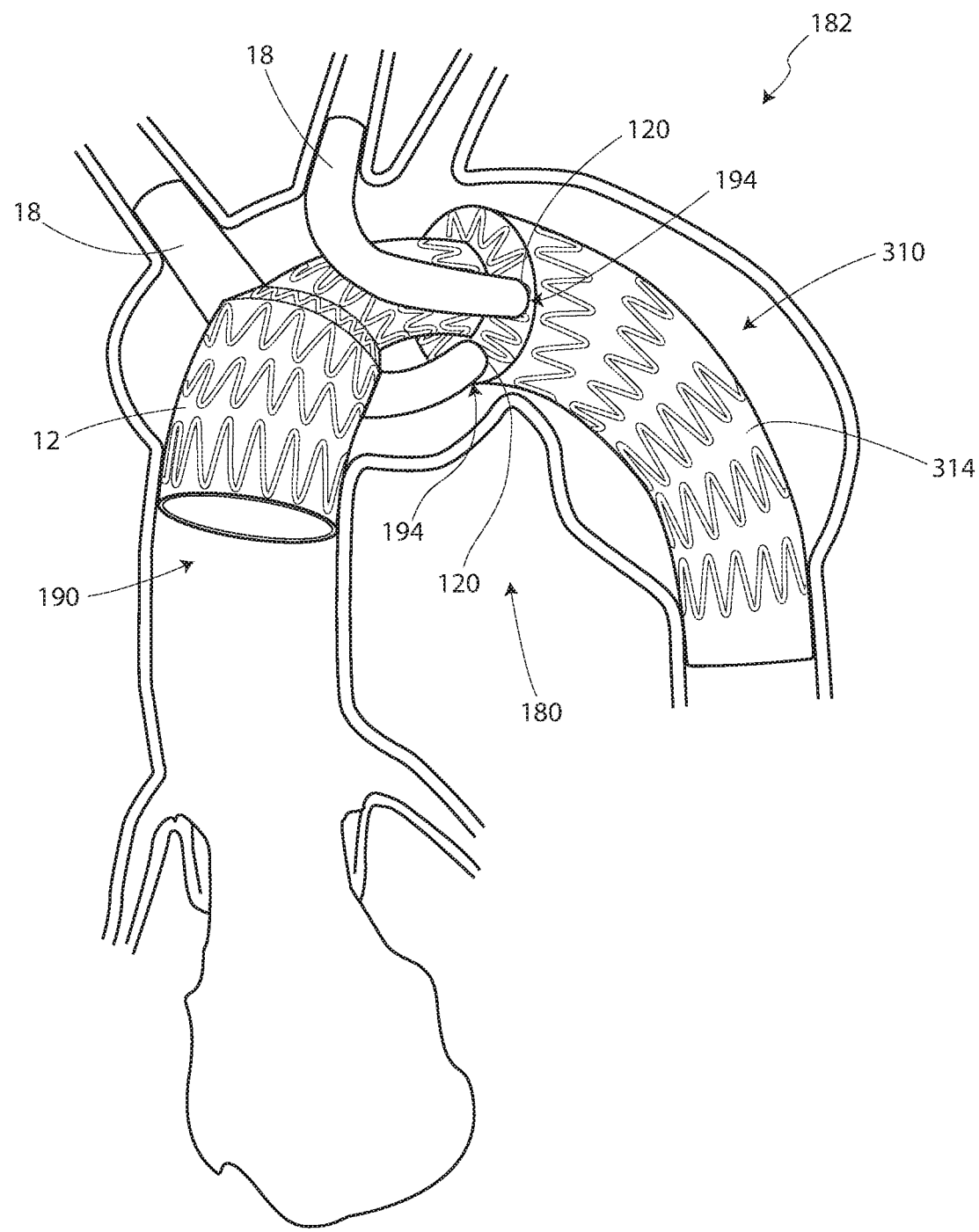
FIG. 13 is a view of the branched aortic graft device of FIG. 12 positioned in an aortic arch.
Figure 14:
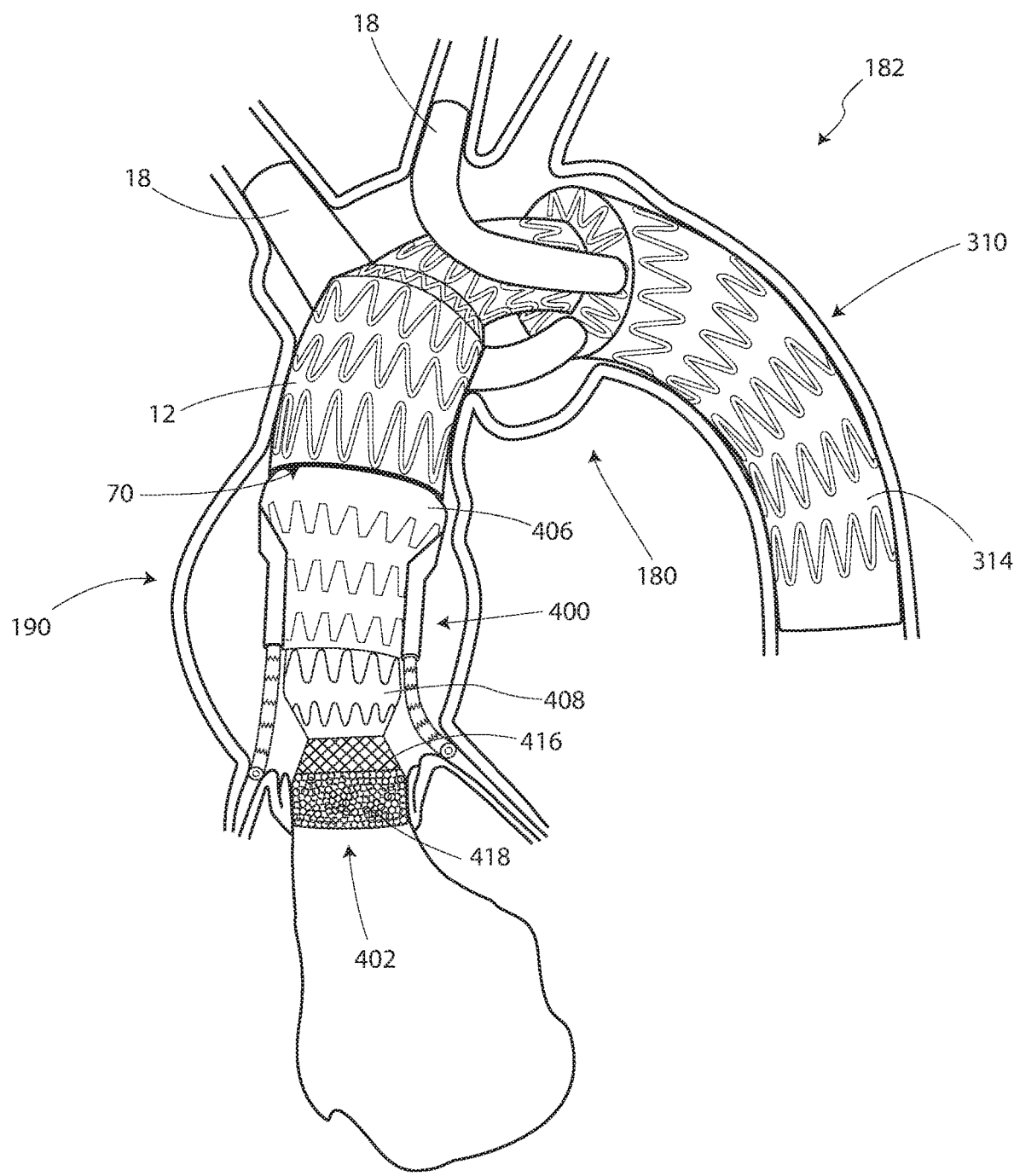
FIG. 14 is a view similar to FIG. 13 showing the branched aortic graft device attached to a transcatheter aortic valve.

Referring now to FIGS. 12-14, another embodiment of prosthetic endograft device (hereinafter device 310) is shown. The embodiment of FIGS. 12-14 includes a number of features that are the same or substantially the same as those described above in regard to the embodiment of FIGS. 1-8. Such features are identified in FIGS. 12-14 with the same reference numbers used in FIGS. 1-8. The device 310 includes a proximal component 12, a distal component 314, and a plurality of branch components 16 attached to the distal component 314.

As shown in FIG. 12, the distal component 314 has a proximal end 316, which is attached to a distal end 26 of the proximal component 12. The distal component 314 also has a distal end 318, which is the distal end of the device 10. The component 314 includes a proximal section 320 that extends from the end 316 to connect to a distal section 322. The distal section 322 extends to the end 318. In the illustrative embodiment, the distal section 322 has a cylindrical outer surface 324, which has a diameter 326 equal to approximately 24 millimeters. It should be appreciated that in other embodiments the diameter 326 may vary based on, for example, the size of the patient's aorta. The distal section 322 has a length equal to approximately 100 millimeters.

The proximal section 320 of the component 314 includes a proximal surface 328 that extends outwardly from a cylindrical outer surface 34 of the proximal component 12. As shown in FIG. 1, the proximal surface 328 extends to an outer edge 330 positioned at the end 316 of the proximal section 320. The edge 330 is connected to the cylindrical outer surface 324 of the distal section 322.

As shown in FIG. 12, the proximal surface 328 of the component 314 has a frustoconical shape that tapers from a diameter 36 to the diameter 326. When the device 310 is viewed as shown in FIG. 12, an angle 332 is defined between the proximal surface 328 and the cylindrical outer surface 34 of the proximal component 12. In the illustrative embodiment, the angle 332 is equal to approximately 135 degrees.

The proximal surface 328, like proximal surface 100 of the component 14 has a plurality of openings 120 defined therein. Each opening 120 in the proximal surface 328 is sized to receive a tubular conduit 18. As shown in FIG. 12, each branch component 16 is positioned in a chamber 72 of the distal component 314 such that the passageway 150 of the branch component 16 is aligned with and covers one of the openings 120 defined in the distal component 314. Each branch component 16 is secured to the distal component 314 in the manner described above in regard to FIGS. 1-8.

As shown in FIG. 13, the device 310 may be used in an arch 180 of a patient's aorta 182. The procedure for inserting the device 310 is similar to the procedure described above for inserting the device 10. Prior to insertion of the device 10, exposure to the common femoral artery (not shown) and the common carotid arteries 184, 186 is performed. A left carotid-subclavian bypass may then be performed. Alternatively, the left subclavian artery 188 is exposed and prepared to receive a tubular stent 18 from the device 310. After the patient is heparinized, a medium stiff wire 192 is placed into the ascending aorta 190. The device 310, which is encased in an outer sheath (not shown) of a delivery system, may be advanced over the wire 192 into the arch 180.

The surgeon or other operator may perform an aortogram to identify the positions of the aortic arch branches for appropriate positioning of components 16 in the arch 180. In the illustrative embodiment, the openings 120 in the distal component 314 are marked with double radio-opaque markers 194 to facilitate radiographic identification of the branch components 16. After performing an aortogram, one of the double radiopaque markers 194 of the device 310 is aligned with opening of the subclavian artery 188. When the device 310 is properly aligned, the device 310 may be initially deployed by unsheathing the outer sheath of the delivery system. As described above, the proximal section 28 of the device 310 remains compressed during the initial deployment. After two of the branch components 16 are cannulated and the tubular stents 18 are inserted into the branch components 16, the proximal section 28 may then be expanded to fully deploy the device 310.

As shown in FIG. 14, the surgeon may utilize the device 310 with another endograft device 400 that includes a transcatheter valve 402 to repair an ascending aortic aneurysm. An exemplary endograft device, including the transcatheter valve, is described in U.S. patent application Ser. No. 13/706,896 entitled "DEVICE FOR ENDOVASCULAR AORTIC REPAIR AND METHOD OF USING THE SAME," which is expressly incorporated herein by reference. As shown in FIG. 14, the device 400 includes a distal component 404 having a frame 406 that is received in the tubular chamber 70 of the proximal component 12 of the device 310. In the illustrative embodiment, the distal component 404 of the device 400 is secured to the proximal component 12 of the device 310 via an interference fit and may be assembled intraoperatively within the patient's ascending aorta 190.

The device 400 also includes a proximal component 408 that includes the transcatheter valve 402. The component 408 includes a dual-frame 410 that extends from a proximal end 412 to a distal end 414 secured to the frame 406 of the distal component 404 via an interference fit. The components 404, 408 may also be assembled intraoperatively within the patient's ascending aorta 190. The dual-frame 410 of the proximal component 408 includes a self-expanding outer frame 416 and a balloon-expandable inner frame 418 that is secured to the self-expanding outer frame 416 and houses the valve 402.

The valve 402 is positioned at the proximal end 412 of the component 408. In the illustrative embodiment, the valve 402 is configured as a bicuspid valve. It should be appreciated that in other embodiments the valve 402 may be tricuspid or quadracuspid. The valve 402 may be constructed from treated bovine pericardium or other suitable proven biological or synthetic material. When the proximal component 408 is implanted into the patient's aorta 190 as shown in FIG. 14, the valve 402 replaces the aortic valve and permits fluid (i.e., blood) to selectively pass from the heart and into a passageway extending through the components 404, 408 of the device 400 and into the device 310.

It should be appreciated that in other embodiments the device 400 or devices similar to the device 400 may be used with the device 210 and the device 10 shown and described above in regard to FIGS. 1-11 to repair ascending aortic aneurysms.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the disclosure and that the method and apparatus within the scope of these claims and their equivalents be covered thereby. In sum, it should be understood that the disclosure is capable of modification and variation and is limited only by the following claims.

The invention claimed is:

1. A vascular prosthetic graft device comprising:
a first component comprising a graft material;
a second component comprising a graft material, wherein the second component is engaged with the first component and defines a radially outwardly extending shoulder that extends outwardly of a major diameter of one of the first component or the second component, and wherein the shoulder, in a fully deployed state of the graft device, has a right frustoconical shape;
wherein at least one of the first and second components is supported by wire frame material;
a first stent member;
wherein a first opening is defined on the shoulder for receiving one end of the first stent member,
a second stent member;
wherein a second opening is defined on the shoulder for receiving one end of the second stent member;
wherein a second end of the first stent member is adapted to be received within the brachiocephalic artery,
wherein a second end of the second stent member is adapted to be received within the left common carotid artery,
wherein the second component, in a region spaced apart from the shoulder, has a major diameter that is about equal to the major diameter of the first component,
wherein the first component has a proximal section and a distal section, with the proximal section of the first component extending from a proximal end of the graft device to connect to the distal section of the first component, and with the distal section of the first component connecting to the shoulder, and wherein the proximal section of the first component, in the fully deployed state of the graft device, has an outer diameter larger than an outer diameter of the distal section of the first component,
wherein the second component has a proximal section and a distal section, with the distal section of the second component extending from a distal end of the graft device to connect to the proximal section of the second component, and wherein the proximal section of the second component comprises a proximal surface defining the shoulder and an outer surface that connects the proximal surface to the distal section of the second component,
wherein the right frustoconical shape of the shoulder tapers from the outer surface to the distal section of the first component, and
wherein the outer surface, in the fully deployed state of the graft device, has a right frustoconical shape that tapers from the shoulder to the distal section of the second component.

2. The graft device according to claim 1, wherein each opening extends into the second component at an angle relative to a horizontal defined through the second component.

3. The graft device according to claim 1, wherein the shoulder extends radially a distance from a horizontal defined through the second component to a position aligned with a major diameter of one portion of the first component.

4. The graft device according to claim 1, wherein the shoulder extends at a non-orthogonal angle relative to a horizontal defined through the second component.

5. The graft device according to claim 1, wherein the second component, in the region spaced apart from the shoulder, is substantially concentric with the first component.

6. The graft device according to claim 1, wherein the proximal section of the first component comprises a main body and a connecting body that connects the main body to the distal section of the first component.

7. The graft device according to claim 6, wherein the connecting body, in an expanded position of the proximal section of the first component, has a right frustoconical shape that tapers from the main body to the distal section of the first component.

8. The graft device according to claim 7, wherein the main body, in the expanded position of the proximal section of the first component, has a cylindrical shape.

9. The graft device according to claim 8, wherein the distal section of the first component, in the expanded position of the proximal section of the first component, has a cylindrical shape.

10. The graft device according to claim 6, wherein the connecting body, the distal section of the first component, and the shoulder define an annular compartment in the fully deployed state of the graft device.

11. The graft device according to claim 10, further comprising a mesh cage that encloses the annular compartment in the fully deployed state of the graft device, wherein the mesh cage comprises a plurality of openings for receiving the first stent member and the second stent member.

12. The graft device according to claim 1, wherein the distal section of the second component, in the fully deployed state of the graft device, has a cylindrical shape.

13. The graft device according to claim 1, wherein the first opening and the second opening are circumferentially spaced apart from one another.

14. The graft device according to claim 1, further comprising:
a first branch component attached to the second component and positioned in a chamber of the second component, wherein the first branch component defines a first passageway for receiving the one end of the first stent member, and wherein the first passageway is aligned with the first opening; and
a second branch component attached to the second component and positioned in the chamber of the second component, wherein the second branch component defines a second passageway for receiving the one end of the second stent member, and wherein the second passageway is aligned with the second opening.

15. The graft device according to claim 14, wherein each of the first branch component and the second branch component is secured to an inner surface of the second component.

16. The graft device according to claim 14, wherein each of the first branch component and the second branch component comprises:
a proximal frame;
a distal frame spaced apart from the proximal frame; and
an outer layer that couples the proximal frame to the distal frame.

* * * * *